(12) United States Patent
Iacobelli

(10) Patent No.: US 8,679,495 B2
(45) Date of Patent: Mar. 25, 2014

(54) USE OF ANTI-90K MONOCLONAL ANTIBODIES FOR THE PREVENTION AND TREATMENT OF TUMORS AND METASTASES THEREOF

(75) Inventor: Stefano Iacobelli, Rome (IT)

(73) Assignee: MediaPharma S.r.l., Chieti (IT)

( * ) Notice: Subject to any disclaimer, the term of this patent is extended or adjusted under 35 U.S.C. 154(b) by 171 days.

(21) Appl. No.: 13/203,280

(22) PCT Filed: Feb. 18, 2010

(86) PCT No.: PCT/IT2010/000060
§ 371 (c)(1),
(2), (4) Date: Sep. 20, 2011

(87) PCT Pub. No.: WO2010/097825
PCT Pub. Date: Sep. 2, 2010

(65) Prior Publication Data
US 2012/0003157 A1    Jan. 5, 2012

(30) Foreign Application Priority Data
Feb. 25, 2009  (IT) .............................. RM2009A0081

(51) Int. Cl.
*A61K 39/395*  (2006.01)

(52) U.S. Cl.
USPC ...................................... 424/133.1; 435/7.23

(58) Field of Classification Search
None
See application file for complete search history.

(56) References Cited

U.S. PATENT DOCUMENTS 5,298,391 A * 3/1994 Iacobelli .......................... 435/5
7,160,736 B2 * 1/2007 Niehaus et al. ............... 436/525

FOREIGN PATENT DOCUMENTS

WO  93/16180 A2  8/1993
WO  2007/074966 A1  7/2007

OTHER PUBLICATIONS

Ezzell (J. NIH Res. 1995 7:46).*
Spitler (Cancer Biotherapy, 1995, 10:1-3).*
Boon (Adv. Can. Res. 1992 58:177-210).*
Iacobelli et al Breast Cancer Research vol. 11p. 19 (1988).*
Koths et al JBC vol. 268 p. 14245 (1993).*
Iacobelli et al Cancer Research vol. 46 p. 3005 (1986).*
Ozaki Y et al "Identification of antigenic epitopes recognized by Mac-2 binding protein—specific cytotoxic T lymphocytes for use in cancer immunotherapy"—Biochemical and Biophysical Research Communications, Academic Press Inc. Orlando, FL, US, vol. 317, No. 4, May 14, 2004, pp. 1089-1095, XP004502880, ISSN: 0006-291X the whole document.
Ulmer Tricia A et al., "Tumor-associated antigen 90K/Mac-2-binding protein: Possible role in colon cancer" Journal of Cellular Biochemistry, vol. 98, No. 5, Aug. 2006, pp. 351-1366, XP002545567ISSN: 0730-2312 the whole document.
Tinari Nicola, et al: "Identification of the tumor antigen 90K domains recognized by monoclonal antibodies SP2 and L3 and preparation and characterization of novel anti-90K monoclonal antibodies" Biochemical and Biophysical Research Communications, Academic Press, San Diego, CA; US, vol. 232, No. 2, Jan. 1, 1997, pp. 367-372, XP002506185 ISSN: 0006-291X the-whole document.
Tinari Nicola et al., "High expression of 90K (Mac-2 BP) is associated with poor survival in node-negative breast cancer patients not receiving adjuvant systemic therapies" International Journal of Cancer, vol. 124, No. 2, Jan. 2009,pp. 333-338, XP002545568 ISSN: 0020-7136 the whole document.

* cited by examiner

*Primary Examiner* — Sheela J Huff
(74) *Attorney, Agent, or Firm* — Rothwell, Figg, Ernst & Manbeck, P.C.

(57) ABSTRACT

The present invention relates to the use of anti-90K monoclonal antibodies for prevention and treatment of tumors and metastases thereof. In particular, the invention relates to the use of anti-90K monoclonal antibodies able to inhibit the adhesive processes of tumor cells and angiogenesis in tumors such as breast cancer, ovarian cancer, lung cancer, gastrointestinal cancer, melanoma, lymphoma and other tumors overexpressing 90K.

7 Claims, 5 Drawing Sheets

USE OF ANTI-90K MONOCLONAL ANTIBODIES FOR THE PREVENTION AND TREATMENT OF TUMORS AND METASTASES THEREOF

CROSS REFERENCE TO RELATED APPLICATION

This application is a 35 U.S.C. 371 National Phase Entry Application from PCT/IT2010/000060, filed Feb. 18, 2010, which claims the benefit of Italian Patent Application No. RM2009A000081 filed on Feb. 25, 2009, the disclosure of which is incorporated herein in its entirety by reference.

The present invention concerns the use of anti-90K monoclonal antibodies for prevention and treatment of tumors and metastases thereof. In particular, the invention relates to the use of anti-90K monoclonal antibodies able to inhibit the adhesive processes of tumor cells and the angiogenesis in tumors such as breast cancer, ovarian cancer, lung cancer, gastrointestinal cancer, melanoma, lymphoma and other tumors overexpressing 90K.

Tumor is a disease characterized by an uncontrolled proliferation of the cells that form it, called malignant cells, able to invade adjacent tissues and spread in other parts of the human body through a process known as metastatization. The term tumor will be used therein to indicate a malignant tumor, also known as cancer.

In almost all cases, tumors that have developed metastases cause death of affected patients in a time ranging from few months to some years.

Most of the drugs used in the treatment of tumors are cytotoxic chemotherapeutic agents (also called antiblastic agents or just chemotherapeutic agents). These drugs act by damaging DNA or by inhibiting cell division and, thereby, induce cell death in a non specific manner. In this way, they kill both tumor and normal cells, especially those that are in a proliferative phase. The lack of specificity in the mechanisms of action of chemotherapeutic agents is responsible for the severe toxicity following their administration.

In the last decade, the scientific research has considerably improved the knowledge on the molecular mechanisms underlying the transformation of normal cells into tumor cells and the molecular mechanisms involved in the formation of metastases. This new knowledge has led to the development of drugs defined as "targeted". These drugs have been designed to act specifically against tumor cells carrying a particular molecular and/or functional defect responsible for uncontrolled proliferation and/or metastases formation.

Although less often and less severe than those observed with chemotherapeutic drugs, side effects do occur even with targeted agents. Moreover, like chemotherapeutic drugs, targeted agents can control the disease only temporarily because of the onset of resistance.

Despite scientific progress and the introduction in clinical practice of novel chemotherapeutic and targeted agents, cancer remains a disease difficult to cure, responsible for about 13% of all deaths worldwide [1]. Almost 90% of the deaths caused by cancer is due to the spread of a metastatic disease [2].

In light of the above considerations, it is clear that new, more effective, and possibly less toxic anti-tumor treatments are needed.

It is well known that a cancer can diffuse by local or contiguous extension, or can spread out to form distant metastases. In the latter way, tumor cells leave the primary site and diffuse in the body through pre-existent ducts, such as blood and lymphatic vessels [3]. Tumor cells can survive in the bloodstream through the capability to form aggregates among themselves (homotypic adhesion) [4] or with other cells, like platelets (heterotypic adhesion) [5], generating the so-called "neoplastic embolus". It is also known that tumor cells, in order to diffuse, need to interact with proteins of the extra-cellular matrix (ECM), such as fibronectin, collagen and laminin [6]. The adhesion process between tumor cells and ECM components is mediated, at a molecular level, by membrane proteins known as integrins [7].

In 1986, Iacobelli et al. [8] identified in the culture medium of human breast cancer cells a high molecular weight protein, constituted by subunits of 90.000 daltons and, therefore, named 90K. The protein, also known as Mac-2 BP or LGALS3BP, contains several carbohydrate chains and is organized in different functional domains [8-10]. 90K is detectable inside the cells from which it is secreted. Outside the cell, the protein is detectable in the ECM [11]. 90K is present in biological fluids, including blood, saliva, breast milk and tears, at a concentration of few microgram/ml [10, 12, 13].

Experimental evidences indicate that 90K plays a role in the adhesive processes of tumor cells. For example, the addition of a certain amount of human recombinant 90K to human melanoma cell line A375, maintained in a culture flask as unicellular suspension, determines an increase of cell-cell adhesion (named homotypic adhesion), leading to formation of multicellular aggregates [14]. This effect, which is due to the ability of 90K to bind residues of galectin-3 and galectin-1 harbored on the membrane of adjacent melanoma cells [14, 15], may be relevant during the metastatic spread of tumors. In fact, as mentioned above, tumor cells that detach from the primary tumor and enter blood vessels and/or lymphatic vessels can survive longer if they adhere all together, forming multicellular aggregates [4].

Studies have reported that 90K is able to specifically bind some ECM proteins, including collagen, fibronectin and laminin [11, 16]. In addition, different types of tumor cells start "spreading" as soon as they establish a contact with 90K, similarly to what is observed when cells adhere to the ECM protein laminin [11]. The cellular receptor of 90K responsible for adhesion and spreading has been identified as beta-1 integrin [11].

Tumor cell adhesion to ECM proteins not only favors the processes of migration and cell diffusion, but also preserves cells against apoptosis (also called programmed cell death) caused by antiblastic drugs [17, 18]. Our group observed that when lymphoma tumor cells are maintained in a flask coated with 90K, a binding between the protein and the beta-1 integrin of lymphoma cells takes place and, as a consequence, cells become resistant to the action of antiblastic drugs, as indicated by the reduction of apoptotic cell rate [19]. The protective effect of 90K against antiblastic drug induced apoptosis can explain the poor response to chemotherapy and the reduced survival observed in patients affected by lymphoma with elevated blood levels of 90K [19-21].

As a consequence of the above observations, the pro-adhesive properties of 90K may have an important role in two fundamental steps of the metastatic process: cell to cell adhesion and cell to ECM adhesion [3, 6].

The role of 90K on the promotion of tumor growth and progression is corroborated by several studies showing a relationship between the concentration of protein in the blood or in the tumor cells and patients' response to anti-tumor treatment or prognosis. Using an immuno-enzymatic assay, the concentration of 90K was measured in the blood of patients affected by different types of tumors [13]. Blood concentrations above the normal cut-off level were observed in patients with breast cancer, ovarian cancer, lung cancer, gastro-intestinal cancer, melanoma and lymphoma [13]. Patients affected by breast cancer [22] or ovarian cancer [23] with 90K levels higher than normal cut-off had a shorter survival compared to patients with normal 90K levels. Similarly, in patients affected by Hodgkin or non-Hodgkin lymphoma, high blood levels of 90K were associated with shorter survival and reduced sensitivity to chemotherapy [19-21]. The poor prognostic value of 90K in patients affected by cancer was observed even when the amount of protein was evaluated in tumor tissue, using immunohistochemical procedures. In patients with non-small cell lung cancer [24] or in those with breast cancer [25], high expression levels of the protein in the tumor cells were associated with a shorter survival. Moreover, similarly to what observed in the case of blood 90K [22], high levels of the protein in tumor cells were associated with a higher propensity of the disease to metastasize [24, 25].

All together, experimental and clinical data indicate that 90K, as a result of its ability to promote adhesion, plays a role in tumor growth and progression. For this reason, the manufacture of agents able to inhibit the pro-adhesive function of this protein may be useful for prevention and/or treatment of cancer.

A revision of international scientific literature has revealed that 90K has never been considered a possible target for anti-cancer treatment on the basis of its specific function, i.e. promotion of cell to cell or cell to ECM adhesion. On the other hand, it has just been hypothesized that an anti-tumor effect can be obtained using an anti-90K vaccine that is capable of eliciting a T-cytotoxic immune response against 90K-expressing cells [26]. This hypothesis, therefore, does not include the use of inhibitors of the specific functions of 90K.

Unexpectedly, the author of the present invention has found that it is possible to inhibit tumor growth by using a specific antibody against 90K, i.e. the monoclonal antibody SP-2, not because it activates an immune response, but rather because it inhibits the pro-adhesive function of 90K. As will be evident later, SP-2 antibody is functionally unique among anti-90K monoclonal antibodies. In fact, differently from other anti-90K monoclonal antibodies available in our laboratories, e.g. those produced by hybridoma 1A4.21, 2A9.44 and 3C12 [27] and the antibody 2A9.41 that is a subclone of 2A9.44, SP-2 antibody is able to inhibit both tumor cell homotypic adhesion and tumor cell adhesion to 90K (see examples 1 and 2). Moreover, SP-2 antibody can significantly delay the growth of human tumors in animal models (see examples 3 and 4) and reduce neoangiogenesis, the process of new blood vessel formation that accompanies and decisively contributes to tumor growth and progression (see example 5).

SP-2 antibody was developed according to the hybridoma procedure of Kohler and Milstein [28], by the immunization of BALB/c mice with proteins released in the culture medium by human breast cancer cells [8]. It is an antibody of IgG1 isotype that specifically recognizes 90K. This antibody has been used for the manufacture of an enzyme-linked immunosorbent assay (ELISA) kit to measure 90K in biological fluid [12, 13]. The antibody was patented as a reagent to determine the concentration of 90K in vitro, for diagnosis and prognosis of patients affected by HIV infection (U.S. Pat. No. 5,298, 391). The murine hybridoma cell line from which SP-2 is purified, was deposited by Stefano Iacobelli at the DSMZ (DEUTSCHE SAMMLUNG VON MIKROORGANISMEN UND ZELLKULTUREN GmbH), Mascheroder Weg 1 B D-3300 Braunschweig, Germany under the Budapest Treaty, accession number DSM ACC2116, on Feb. 5, 1993, and at the C.N.C.M. (Collection Nationale de Cultures de Microorganismes), Pasteur Institute of Paris, France, accession number I-1083.

The present invention pertains to the use of an antibody able to bind 90K protein or 90K-antigen binding region thereof, said antibody or binding region being able to recognize a conformational epitope between residues 107 and 435 of the aminoacid sequence of the 90K protein, for the preparation of a pharmaceutical composition for preventing or treating solid tumors and metastases thereof. According to the invention, the antibody may be a human antibody, a humanized antibody, a bi-specific antibody or a chimeric antibody. Moreover, the antibody may consist of Fab, Fab'2, scFv, SMIP, affibody, avimer, nanobody or "domain antibody".

The antibody or antigen binding region may be administered via endovenous, intramuscular or subcutaneous route.

A preferred embodiment of the present invention pertains to a preparation where the antibody is the SP-2 antibody produced by hybridoma DSM ACC 2116. The DSM ACC 2116 monoclonal antibody SP-2 is produced according to the procedures described by Kohler and Milstein [28], but it may be produced also according to the recombinant DNA technique, using the specific nucleotide sequence of SP-2 or a part thereof.

Tumors to be treated may be selected from the group of tumors with increased 90K production, e.g. those selected from the group consisting of breast cancer, ovarian cancer, lung cancer, gastrointestinal cancer, melanoma, lymphoma and metastases thereof. In all these tumors, higher levels of 90K are associated with a faster progression of the disease, shorter survival of the affected patients and reduced response to antiblastic treatment. Therefore, inhibition of the pro-adhesive functions of the 90K protein, achieved by using SP-2 antibody, may give a benefit to the patients. However, it is not possible to exclude that a SP-2-based treatment can be useful in patients affected by other types of tumors expressing high levels of 90K.

A further embodiment of the present invention pertains to a pharmaceutical composition constituted of or comprising, as active agents, the antibody or antigen binding region, as defined above, in combination with one or more anti-tumor agents, along with one or more pharmaceutically acceptable excipients and/or adjuvants. The anti-tumor agent may be selected from the group consisting of an antibody, an antimetabolite, a vinca alkaloid, a taxane, an anthracycline, a platin derivative, a small molecule, a kinase inhibitor, an alkylating agent, a mTOR inhibitor. Examples of anti-tumor agents are the following: docetaxel, paclitaxel, doxorubicin, farmorubicin, cyclophosphamide, 5-fluorouracil, vinorelbine, cisplatin, carboplatin, trastuzumab, bevacizumab, cetuximab, panitumumab, sunitinib, sorafenib, gefitinib, erlotinib, temsirolimus.

In another embodiment, the present invention pertains to the use of the above defined composition for the manufacture of a medication for preventing or treating tumors and metastases thereof.

In yet another embodiment, the present invention pertains to a method for the recognition of 90K-producing tumors, based on the contact of patient tumor cells with the SP-2 antibody or antigen binding region thereof as defined above. To this purpose, the antibody can be used unlabeled or labeled with a chromogen, a fluorochrome, or a radioactive isotype, and can be used for immunohistochemistry or in vivo molecular imaging. Examples of tumors to be recognized are, but not exclusively, those selected from the group that frequently exhibits high expression levels of 90K, e.g. breast cancer, ovarian cancer, lung cancer, gastrointestinal cancer, melanoma and lymphoma.

A final embodiment of the present invention relates to a kit for diagnosis in vitro of a 90K-producing tumor consisted of or comprising SP-2 antibody or antigen binding region thereof as defined above.

The present invention will be now described, for illustrative but not limitative purposes, according to its preferred embodiments, with particular reference to the enclosed figures.

Figure 5:
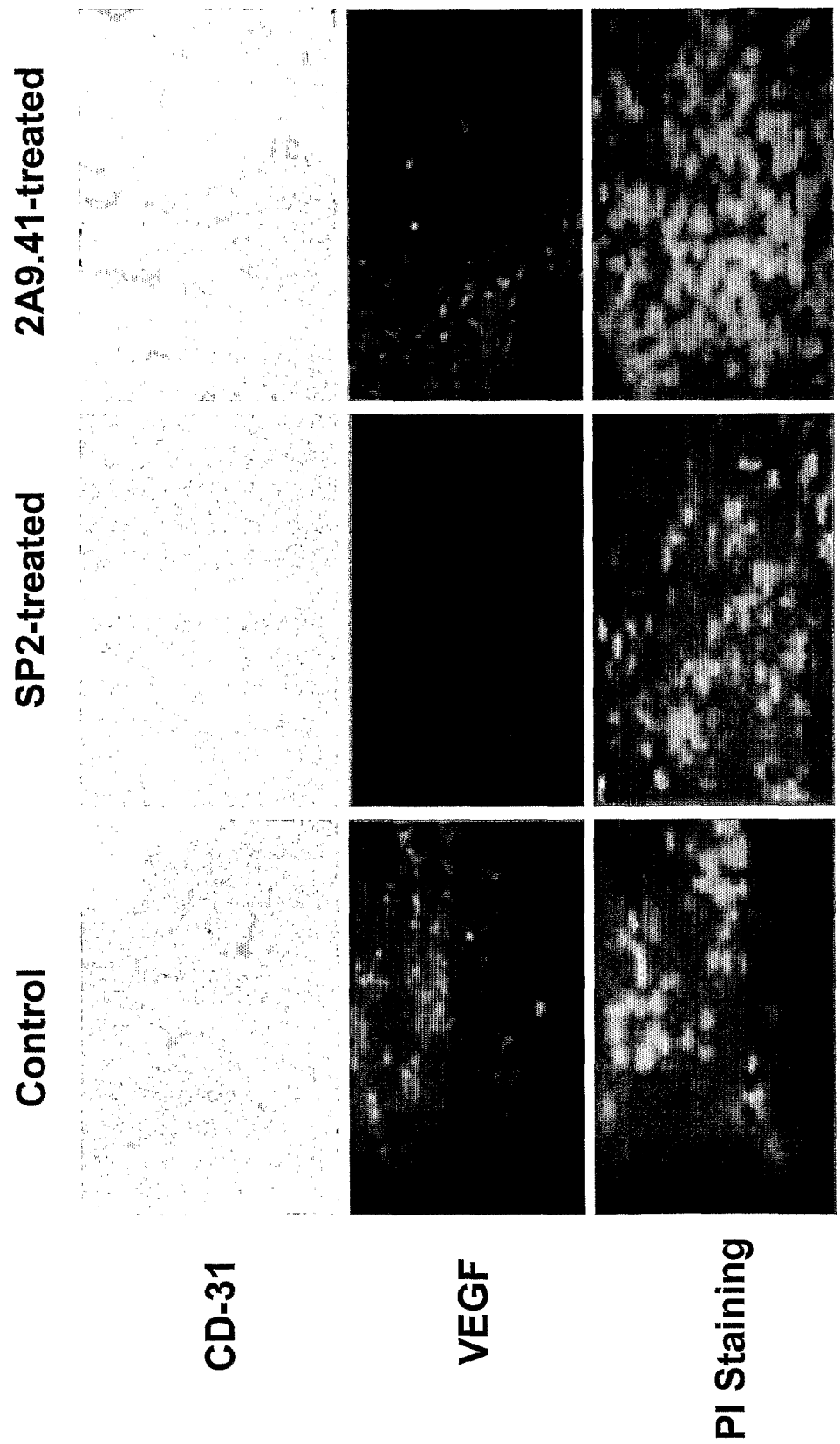

FIG. 5 shows the expression levels of angiogenesis as evaluated by the assessment of CD-31 and Vascular Endothelial Growth Factor (VEGF), evaluated by immunohistochemistry and immunofluorescence, respectively, in tumors derived from human breast cancer cells MDA-MD-231 grown in nude mice of the control group (receiving phosphate buffer), in those treated with SP-2 antibody or in those treated with 2A9.41 antibody.

EXAMPLE 1

Ability of SP-2 Antibody to Inhibit the 90K-Induced Homotypic Adhesion of Melanoma Cells Materials and methods: Human melanoma cells A375 were maintained in polypropylene tube as unicellular suspension in PBS (0.5 ml), at a concentration of $1\times10^6$ cells/ml, and kept stirring at 100 rpm, 37° C., in presence of purified recombinant 90K (10 μg/ml), with or without the addition of SP-2 or other anti-90K antibodies (1A4.21, 2A9.41, 2A9.44, 3C12) at a concentration of 10 μg/ml.

After 1 hour, cell aggregation was stopped by adding 50 μl of 10% paraformaldehyde. The number of aggregates was calculated by difference, i.e. counting single cells at the microscope.

Figure 1:
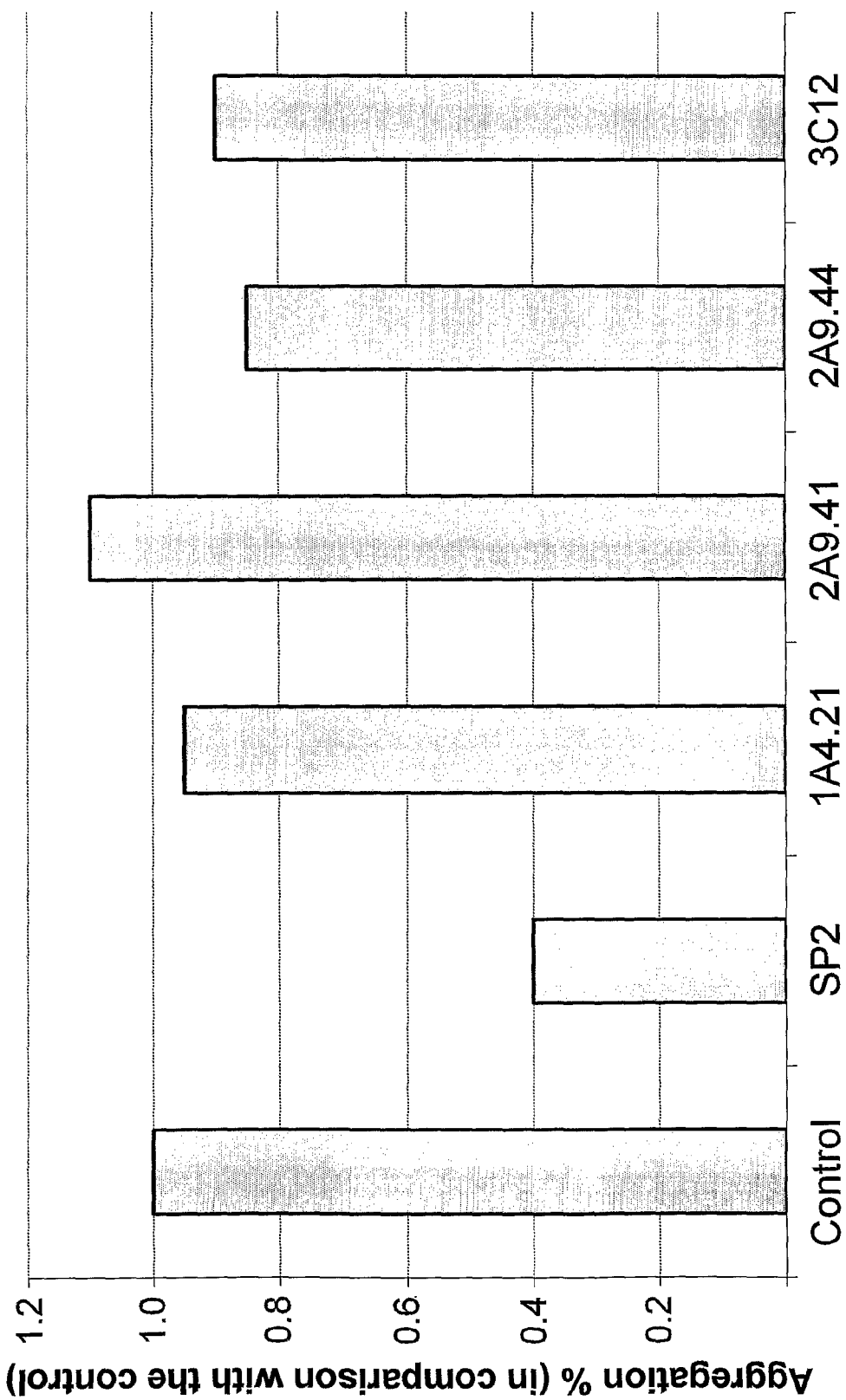
FIG. 1 shows percentages of cell aggregation after treatment with different anti-90K monoclonal antibodies.

Results: A significant reduction of cell aggregation was observed when SP-2, but not other anti-90K antibodies, was added to A375 cells (FIG. 1).

EXAMPLE 2

Ability of SP-2 Antibody to Inhibit Adhesion of Melanoma Cells to 90K

Materials and methods: Wells of a 96-well microtiter plate were coated with 90K by incubating the plate overnight at 4° C. with 100 μl/well of a 10 μg/ml solution of 90K in PBS. To perform the adhesion assay, exceeding protein in the wells was aspirated, and the plate saturated with 1% BSA in PBS (100 μl/well) at 37° C. for 1 hour. Then, BSA was washed out and PBS (control) or different anti-90K antibodies (SP-2, 1A4.21, 2A9.41, 2A9.44, 3C12), at a concentration of 10 μg/ml in PBS, were added into the wells (100 μl/well). After 1 hour incubation at 37° C., the wells were washed four times with PBS and an unicellular suspension (100 μl) of human melanoma cell MEL 8863, at a concentration of 500,000 cells/ml in serum-free culture medium, was added to each well (50,000 cells/well). After 1 hour at 37° C., the plate was gently washed with PBS and adherent cells were fixed in ethanol for 10 minutes. After staining with crystal violet for 30 minutes and four washes with PBS, the dye was solubilized with 0.25% Triton X-100 and the absorbance at 490 nm assessed by a spectrophotometric microtiter reader.

Figure 2:
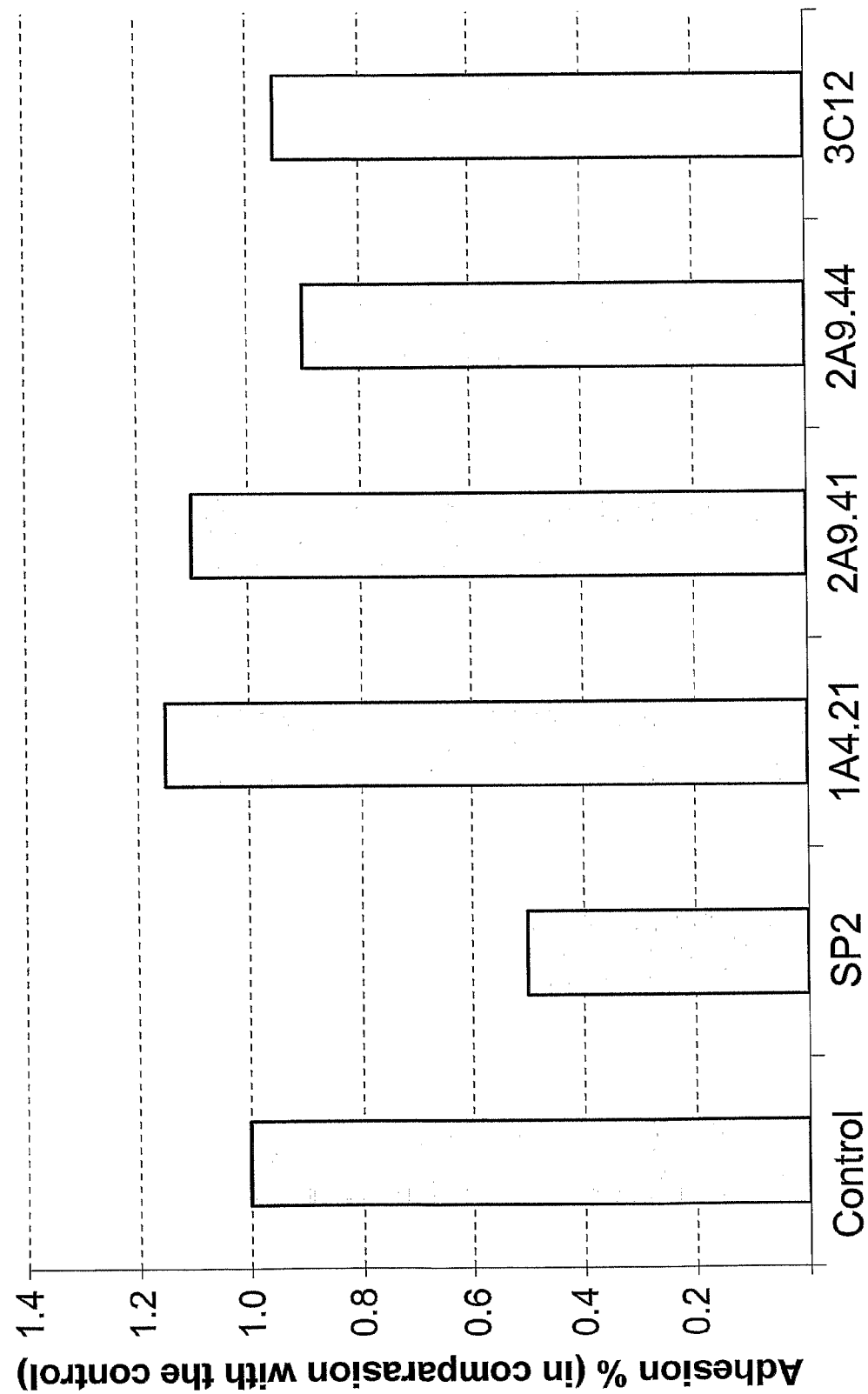
FIG. 2 shows percentages of cell adhesion after treatment with different anti-90K monoclonal antibodies.

Results: A significant reduction of cell adhesion to 90K was observed when SP-2, but not other anti-90K antibodies, was added to the plate (FIG. 2).

EXAMPLE 3

Ability of SP-2 Antibody to Reduce Tumor Growth of Melanoma Cells

Materials and methods: Nude mice were injected subcutaneously with $5\times10^6$ human melanoma cell MEL 8863 (cells expressing 90K) and distributed in three groups. One group was treated with phosphate buffer and served as a control, one group was treated with SP-2 and one group was treated with 2A9.41. Both phosphate buffer and the antibodies were administrated by intraperitoneal route. Antibodies were administered at a dose of 10 μg/kg twice a week. Tumor growth was followed up by measuring lesion diameters up to 33 days after injection. Each group, control and treated, consisted of 8 animals.

Figure 3:
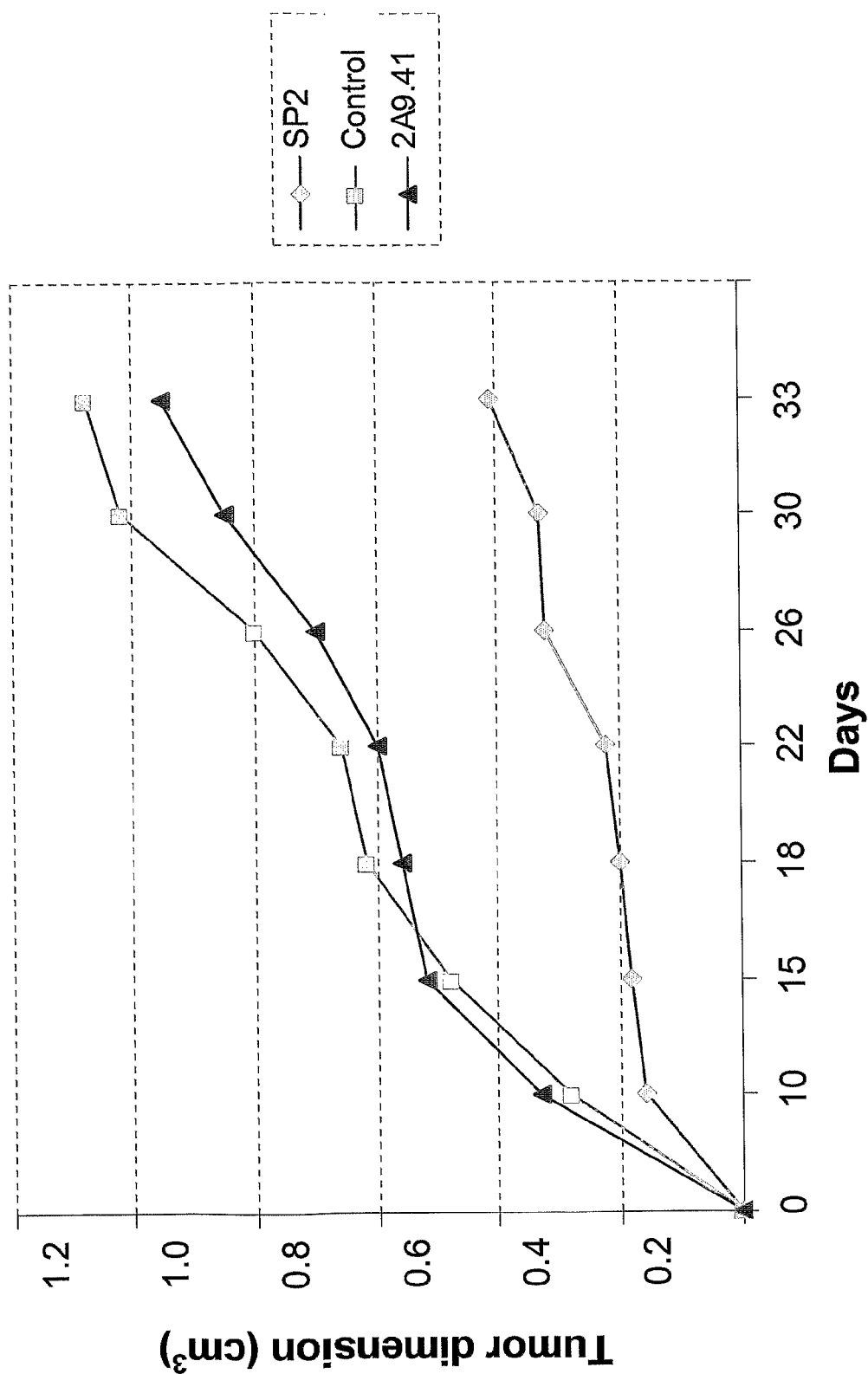
FIG. 3 shows time-dependent size variations of tumors grown in nude mice after injection of human melanoma cells in animals of control group (receiving phosphate buffer), in those treated with SP-2 antibody or in those treated with an anti-90K antibody, termed 2A9.41.

Results: Mice treated with SP-2, but not mice treated with 2A9.41, developed tumors almost 60% smaller than those of the control group (0.4 cm$^3$ vs 1 cm$^3$) (FIG. 3).

EXAMPLE 4

Ability of SP-2 Antibody in Combination with Docetaxel to Reduce Tumor Growth of Breast Cancer Cells Materials and methods: Nude mice were injected subcutaneously with $5\times10^6$ human breast cancer cell MDA-MD-231 (cells expressing 90K). One group was injected by intraperitoneal route with phosphate buffer and served as a control. Other groups were treated by intraperitoneal route with SP-2 antibody at a dose of 10 μg/kg twice a week, or a control IgG at the same dose, or with docetaxel at a dose of 7.5 mg/kg once a week, or with a combination of SP-2 and docetaxel. Tumor growth was followed up by measuring lesion diameters up to 44 days after injection. Each group, control and treated, consisted of 8 animals.

Figure 4:
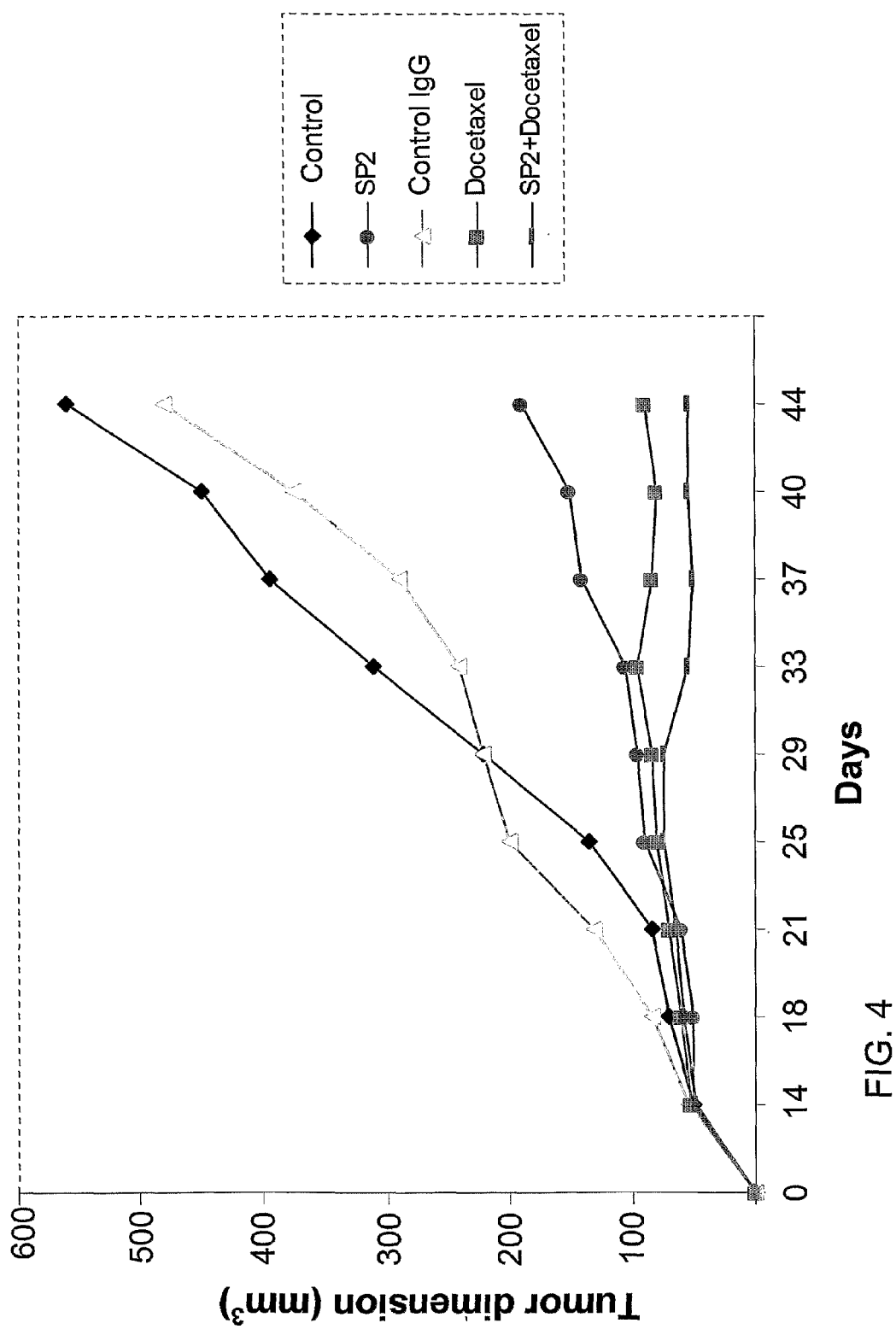
FIG. 4 shows time-dependent size variations of tumors grown in nude mice after injection of human breast cancer cells MDA-MD-231 in animals of the control group (receiving phosphate buffer), in those treated with mouse immunoglobulin (IgG), or in those treated with SP-2 antibody alone or in combination with the anti-tumor agent docetaxel.

Results: Both SP-2 antibody and anti-tumor agent docetaxel significantly reduced tumor growth in comparison with control group. This effect was higher when the two agents were used in combination (FIG. 4).

EXAMPLE 5

Ability of SP-2 Antibody to Reduce the Formation of Blood Vessels and VEGF Production in Tumor Arisen from Breast Cancer Cells in Nude Mice Materials and methods: Nude mice were injected subcutaneously with $5\times10^6$ human breast cancer cell MDA-MD-231 (cells expressing 90K). One group was treated with phosphate buffer by intraperitoneal route and served as a control. Other groups were treated by intraperitoneal route with SP-2 antibody or 2A9.41 at a dose of 10 μg/kg twice a week (as seen in example 3). Each group consisted of 8 animals. After 30 days, animals were sacrificed and tumors removed for making up histological sections. The presence of blood vessels in the tumor tissue was evaluated by immunohistochemistry using an antibody anti-CD31, a glycoprotein expressed in endothelial cells. Tumor VEGF expression was evaluated using an anti-VEGF antibody. Propidium iodide fluorescence (PI staining) was used as control.

Results: Animals treated with SP-2, but not those treated with 2A9.41, developed scanty vascularized tumors, as indicated by a low CD31 expression and absence of VEGF (FIG. 5).

BIBLIOGRAPHY

1. World Health Statistics, World Health Organization, 2008
2. Mehlen P, Puisieux A. Metastasis: a question of life or death. Nat Rev Cancer 2006; 6:449-58]
3. Chambers A F, Groom A C, MacDonald I C. Dissemination and growth of cancer cells in metastatic sites. Nat Rev Cancer 2002; 2:563-72.
4. Updyke T V, Nicolson G L. Malignant melanoma cell lines selected in vitro for increased homotypic adhesion properties have increased experimental metastatic potential. Clin Exp Metastasis 1986; 4:273-284.
5. Nash G F, Turner L F, Scully M F, Kakkar A K. Platelets and cancer. Lancet Oncol 2002; 3:425-430.
6. Gupta G P, Massagué J. Cancer metastasis: building a framework. Cell 2006; 127:679-9.
7. Hood J D, Cheresh D A. Role of integrins in cell invasion and migration. Nat Rev Cancer 2002; 2:91.
8. Iacobelli S, Arnò E, D'Orazio A, Coletti G. Detection of antigens recognized by a novel monoclonal antibody in tissue and serum from patients with breast cancer. Cancer Res 1986; 46:3005-10.
9. Koths K, Taylor E, Halenbeck R, Casipit C, Wang A. Cloning and characterization of a human Mac-2-binding protein, a new member of the superfamily defined by the macrophage scavenger receptor cysteine-rich domain, J Biol Chem 1993; 268:14245-9.
10. Ullrich A, Sures I, D'Egidio M, Jallal B, Powell T J, Herbst R, Dreps A, Azam M, Rubinstein M, Natoli C, et al. The secreted tumor-associated antigen 90K is a potent immune stimulator. J Biol Chem 1994; 269:18401-7.
11. Sasaki T, Brakebusch C, Engel J, Timpl R. Mac-2 binding protein is a cell-adhesive protein of the extracellular matrix which self-assembles into ring-like structures and binds b1 integrins, collagens and fibronectin. EMBO J 1998; 17:1606-13.
12. D'Ostilio N, Sabatino G, Natoli C, Ullrich A, Iacobelli S. 90K (Mac-2 BP) in human milk, Clin Exp Immunol 1996; 104:543-6.
13. Iacobelli S, Arno E, Sismondi P, Natoli C, Gentiloni N, Scambia G, Giai M, Cortese P, Panici P B, Mancuso S. Measurement of a breast cancer associated antigen detected by monoclonal antibody SP-2 in sera of cancer patients. Breast Cancer Res Treat 1988; 11:19-30.
14. Inohara H, Akahani S, Koths K, Raz A. Interactions between galectin-3 and Mac-2-binding protein mediate cell-cell adhesion. Cancer Res 1996; 56:4530-4.
15. Grassadonia A, Tinari N, Iurisci I, Piccolo E, Cumashi A, Innominato P, D'Egidio M, Natoli C, Piantelli M, Iacobelli S. 90K (Mac-2 BP) and galectins in tumor progression and metastasis. Glycoconj J 2004; 19:551-6.
16. Ulmer T A, Keeler V, André S, Gabius H J, Loh L, Laferté S. The tumor-associated antigen 90K/Mac-2-binding protein secreted by human colon carcinoma cells enhances extracellular levels of promatrilysin and is a novel substrate of matrix metalloproteinases-2, -7 (matrilysin) and -9: Implications of proteolytic cleavage. Biochim Biophys Acta 2009, [Epub ahead of print]
17. Damiano J S, Cress A E, Hazlehurst L A, Shtil A A, Dalton W S. Cell adhesion mediated drug resistance (CAM-DR): role of integrins and resistance to apoptosis in human myeloma cell lines. Blood 1999; 93:1658.
18. Seth T, Rantoul R, Moore S, et al. Extracellular matrix proteins protect small cell lung cancer cells against apoptosis: a mechanism for small cell lung cancer growth and drug resistance in vivo. Nat Med 1999; 5:662.
19. Fornarini B, D'Ambrosio C, Natoli C, Tinari N, Silingardi V, Iacobelli S. Adhesion to 90K (Mac-2 BP) as a mechanism for lymphoma drug resistance in vivo. Blood 2000; 96:3282-5.
20. Rea A, Calmieri G, Tinari N, Natoli C, Tagliaferro P, Morabito A, Grassadonia A, Bianco A R, Iacobelli S. 90K is a serum marker of poor prognosis in non-Hodgikin's lymphoma patients. Oncol Rep 1994; 723-5.
21. Zhang D S, Jiang W Q, Li S, Zhang X S, Mao H, Chen X Q, Li Y H, Zhan J, Wang F H. Predictive significance of serum 90K/Mac-2BP on chemotherapy response in non-Hodgkin's lymphoma. Ai Zheng 2003; 22:870-3.
22. Iacobelli S, Sismondi P, Giai M, D'Egidio M, Tinari N, Amatetti C, Di Stefano P, Natoli C, Prognostic value of a novel circulating serum 90K antigen in breast cancer, Br J Cancer 1994; 69:172-6.
23. Zeimet A G, Natoli C, Herold M, Fuchs D, Windbichler G, Daxenbichler G, Iacobelli S, Dapunt O, Marth C. Circulating immunostimulatory protein 90K and soluble interleukin-2-receptor in human ovarian cancer, Int J Cancer 1996; 68:34-8.
24. Marchetti A, Tinari N, Buttitta F, Chella A, Angeletti C A, Sacco R, Mucilli F, Ullrich A, Iacobelli S. Expression of 90K (Mac-2 BP) correlates with distant metastasis and predicts survival in stage I non-small cell lung cancer patients, Cancer Res 2002; 62:2535-9.
25. Tinari N, Lattanzio R, Querzoli P, Natoli C, Grassadonia A, Alberti S, Hubalek M, Reimer D, Nenci I, Bruzzi P, Piantelli M, Iacobelli S; Consorzio Interuniversitario Nazionale per la Bio-Oncologia (CINBO). High expression of 90K (Mac-2 BP) is associated with poor survival in node-negative breast cancer patients not receiving adjuvant systemic therapies, Int J Cancer 2009; 124:333-8.
26. Ozaki Y, Kontani K, Teramoto K, Fujita T, Tezuka N, Sawai S, Watanabe H, Fujino S, Asai T, Ohkubo I. Identification of antigenic epitopes recognized by Mac-2 binding protein-specific cytotoxic T lymphocytes for use in cancer immunotherapy. Biochem Biophys Res Commun 2004; 317: 1089-95.
27. Tinari N, D'Egidio M, Iacobelli S, Bowen M, Starling G, Seachord C, Darveau R, Aruffo A Identification of the tumor antigen 90K domains recognized by monoclonal antibodies SP2 and L3 and preparation and characterization of novel anti-90K monoclonal antibodies. Biochem Biophys Res Commun 1997; 232:367-72.
28. Kohler G, Milstein C. Continuous cultures of fused cells secreting antibody of predefined specificity. Nature 1975; 256:495-497.

The invention claimed is:

1. A pharmaceutical composition comprising:
   an antibody able to bind 90K protein or 90K-antigen binding region thereof, said antibody or binding region being able to recognize a conformational epitope within a region between residues 107 and 435 of the amino acid sequence of 90K protein, wherein the antibody is the monoclonal antibody SP-2 produced by hybridoma cell line DSM ACC 2116:
   at least one anti-tumor agent; and
   at least one pharmaceutically acceptable excipient and/or adjuvant.

2. The composition according to claim 1, wherein the anti-tumor agent is selected from the group consisting of an antibody, and antimetabolite, a vinca alkaloid, a taxane, an anthracycline, a platin derivative, a small molecule, a kinase inhibitor, an alkylating agent, and a mTOR inhibitor.

3. The composition according to claim 1, wherein the anti-tumor agent is selected from the group consisting of docetaxel, paclitaxel, doxorubicin, farmorubicin, cyclophosphamide, 5-fluorouracil, vinorelbine, cisplatin, carboplatin, trastuzumab, bevacizumab, cetuximab, panitumumab, sunitinib, sorafenib, gefitinib, erlotinib, and temsirolimus.

4. A method of treating tumors expressing 90K protein or metastases thereof in a patient in need of such treatment, comprising administering to said patient an effective amount of a monoclonal antibody SP-2 produced by hybridoma cell line DSM ACC 2116;
   wherein said antibody is able to bind 90K protein or 90-antigen binding region thereof, and
   wherein said antibody or binding region is able to recognize a conformational epitope within a region between residues 107 and 435 of the amino acid sequence of 90K protein.

5. The method according to claim 4, wherein the tumors are tumors with increased 90K production.

6. The method according to claim 4, wherein the tumors are selected from the group consisting of breast cancer, ovarian cancer, lung cancer, gastrointestinal cancer melanoma lymphoma and metastases thereof.

7. A method for the recognition of a 90K-producing tumor, the method comprising:
   supplying a SP-2 antibody produced by hybridoma cell line DSM ACC 2116 or antigen binding region thereof, wherein the antibody is labeled with a chromogen, a fluorochrome or a radioactive isotype;
   using the antibody or binding region thereof to contact patient tumor cells;
   determining the presence of the SP-2 antibody using in vivo molecular imaging; and
   determining the presence of 90K-producing tumor cells to which the antibody or antigen binding region thereof binds.

* * * * *